United States Patent [19]

Lucey et al.

[11] Patent Number: 5,620,415
[45] Date of Patent: Apr. 15, 1997

[54] SURGICAL INSTRUMENT

[75] Inventors: Paul V. Lucey, Sandown, N.H.; Paul A. Torrie, Marblehead; C. Vaughan Seifert, Boxboro, both of Mass.; Graham Smith, Plaistow, N.H.

[73] Assignee: Smith & Dyonics, Inc., Andover, Mass.

[21] Appl. No.: 319,057

[22] Filed: Sep. 23, 1994

Related U.S. Application Data

[63] Continuation of Ser. No. 11,416, Jan. 29, 1993, abandoned.

[51] Int. Cl.$^6$ .................................................. A61B 17/20
[52] U.S. Cl. ............................ 604/22; 606/170; 606/205; 128/752
[58] Field of Search ................................... 128/751, 752, 128/753, 754; 606/170, 174, 205, 206, 207, 208, 209, 210, 159, 171, 180, 194; 604/22

[56] References Cited

U.S. PATENT DOCUMENTS

| | | | |
|---|---|---|---|
| 274,096 | 5/1883 | Shutt | D24/27 |
| 745,722 | 12/1903 | Freeman . | |
| 1,630,239 | 5/1927 | Binkley et al. . | |
| 1,636,636 | 7/1927 | Humble . | |
| 2,878,809 | 3/1959 | Treace . | |
| 3,342,175 | 9/1967 | Bulloch | 128/754 |
| 3,618,611 | 11/1971 | Urban . | |
| 3,847,154 | 11/1974 | Nordin . | |
| 3,964,468 | 6/1976 | Schulz . | |
| 4,020,847 | 5/1977 | Clark, III . | |
| 4,167,943 | 9/1979 | Banko . | |
| 4,167,944 | 9/1979 | Banko . | |
| 4,203,444 | 7/1987 | Bonnell et al. | 604/22 |
| 4,246,902 | 1/1981 | Martinez . | |
| 4,258,716 | 3/1981 | Sutherland . | |
| 4,265,231 | 5/1981 | Scheller, Jr. et al. . | |
| 4,274,414 | 6/1981 | Johnson et al. . | |
| 4,320,761 | 3/1982 | Haddad . | |

(List continued on next page.)

FOREIGN PATENT DOCUMENTS

| | | |
|---|---|---|
| 2074798 | 7/1992 | Canada . |
| 0393834 | 10/1990 | European Pat. Off. . |
| 0445918 | 9/1991 | European Pat. Off. . |
| 0481760 | 4/1992 | European Pat. Off. . |
| 0538984 | 4/1993 | European Pat. Off. . |
| 3219629 | 12/1983 | Germany . |
| 86007100.9 | 9/1986 | Germany . |
| 3828478 | 5/1989 | Germany . |
| 123563 | 6/1991 | Germany .............................. 606/205 |
| 61-265133 | 11/1986 | Japan . |
| 1235321 | 6/1971 | United Kingdom . |
| WO93/20760 | 10/1993 | WIPO . |

OTHER PUBLICATIONS

United States Surgical Corporation Advertisement, Auto Suture™ STAPLEOSCOPY™ endoscopic instruments, Journal of Laparoendoscopic Surgery, 1992.
The Surgical Armamentarium by American V. Mueller, p. 1030 of Catalog No. 80 1980.

*Primary Examiner*—Michael Powell Buiz
*Assistant Examiner*—Patrick Rasche
*Attorney, Agent, or Firm*—Fish & Richardson P.C.

[57] ABSTRACT

A surgical instrument in which a surgical tool is carried distally of a bend region in a stationary support member by an assembly that transmits proximally applied forces through the bend region to both operate the surgical tool and selectively change the rotational orientation of the surgical tool with respect to the stationary member. In another aspect, in which the stationary member does not include a bend region, a rotatable member supported by the stationary member transmits rotational force to the surgical tool to selectively change the rotational orientation of the tool, and a driver member supported by the stationary member transmits axial force to the surgical tool to operate it. In still another aspect in which the stationary member includes the bend region but the surgical tool is not rotatable, a movable member supported by the stationary member is constructed to transmit a proximally applied axial force through the bend region to operate a surgical tool disposed in a distal region of the instrument.

34 Claims, 6 Drawing Sheets

U.S. PATENT DOCUMENTS

| | | |
|---|---|---|
| 4,433,687 | 2/1984 | Burke et al. . |
| 4,440,170 | 4/1984 | Golden et al. . |
| 4,445,509 | 5/1984 | Auth . |
| 4,466,429 | 8/1984 | Loscher et al. . |
| 4,483,562 | 11/1984 | Schoolman ............................... 294/19 |
| 4,512,344 | 4/1985 | Barber . |
| 4,517,977 | 5/1985 | Frost . |
| 4,522,206 | 6/1985 | Whipple et al. . |
| 4,541,423 | 9/1985 | Barber . |
| 4,545,374 | 10/1985 | Jacobson . |
| 4,576,772 | 3/1986 | Carpenter ............................... 264/154 |
| 4,582,181 | 4/1986 | Samson ................................. 606/194 |
| 4,589,412 | 5/1986 | Kensey . |
| 4,631,052 | 12/1986 | Kensey ................................... 604/22 |
| 4,632,110 | 12/1986 | Sanagi . |
| 4,644,951 | 2/1987 | Bays ....................................... 606/170 |
| 4,646,738 | 3/1987 | Trott . |
| 4,649,919 | 3/1987 | Thimsen et al. . |
| 4,662,371 | 5/1987 | Whipple et al. . |
| 4,669,471 | 6/1987 | Hayashi ................................. 606/205 |
| 4,674,501 | 6/1987 | Greenberg . |
| 4,681,106 | 7/1987 | Kensey et al. . |
| 4,690,140 | 9/1987 | Mecca . |
| 4,696,667 | 9/1987 | Masch ..................................... 604/22 |
| 4,705,038 | 11/1987 | Sjostrom et al. . |
| 4,706,655 | 11/1987 | Krauter ..................................... 128/4 |
| 4,738,256 | 4/1988 | Freeman et al. . |
| 4,760,848 | 8/1988 | Hasson . |
| 4,763,669 | 8/1988 | Jaeger ..................................... 128/751 |
| 4,770,174 | 9/1988 | Luckman et al. . |
| 4,834,729 | 5/1989 | Sjostrom . |
| 4,842,578 | 6/1989 | Johnson et al. ........................... 604/22 |
| 4,858,897 | 8/1989 | Irifune ..................................... 267/181 |
| 4,867,155 | 9/1989 | Isaacson . |
| 4,880,015 | 11/1989 | Nierman ................................. 128/751 |
| 4,938,214 | 7/1990 | Specht et al. ........................... 606/206 |
| 4,945,920 | 8/1990 | Clossick ................................. 128/751 |
| 4,950,273 | 8/1990 | Briggs ..................................... 606/113 |
| 4,982,727 | 1/1991 | Sato . |
| 4,986,825 | 1/1991 | Bays et al. ................................ 604/22 |
| 4,998,527 | 3/1991 | Meyer ........................................ 128/6 |
| 4,998,923 | 3/1991 | Samson et al. ......................... 606/194 |
| 5,009,661 | 4/1991 | Michelson ............................... 606/170 |
| 5,094,247 | 3/1992 | Hernandez et al. .................... 128/751 |
| 5,147,373 | 9/1992 | Ferzli . |
| 5,152,744 | 10/1992 | Krause et al. ............................ 604/22 |
| 5,174,300 | 12/1992 | Bales et al. ............................. 606/205 |
| 5,217,479 | 6/1993 | Shuler ..................................... 606/180 |
| 5,254,130 | 10/1993 | Poncet et al. ........................... 606/206 |
| 5,261,917 | 11/1993 | Hasson et al. .......................... 606/139 |
| 5,290,308 | 3/1994 | Knight ..................................... 606/205 |
| 5,333,502 | 8/1994 | Hassler et al. .......................... 606/205 |

SURGICAL INSTRUMENT

This is a continuation of application Ser. No. 08/011,416, filed Jan. 29, 1993, now abandoned.

CROSS REFERENCE TO RELATED APPLICATION

This application is related to an application entitled, "Surgical Instrument" filed on the same day as this application, assigned to the present assignee, and incorporated herein by reference.

BACKGROUND OF THE INVENTION

This invention relates to surgical instruments, and in particular to arthroscopic surgical instruments.

Surgical instruments such as for arthroscopy typically include a straight, stationary member that distally supports a surgical tool at a fixed rotational position with respect to the axis of the member. Tissue or bone is exposed to the surgical tool through an opening in the distal end of the stationary member. An actuating member is either rotated or reciprocated to operate the surgical tool and cause it to grasp or sever body material (such as tissue or bone). The actuating member is driven either manually by the user or by a motor. The user (e.g., a surgeon) changes the rotational orientation of the surgical tool by manually rotating the instrument. In some instruments in which the tool cuts tissue, severed body material and irrigation fluid are withdrawn from the surgical site through a transport passage in the actuating member (or through another device) in response to applied suction.

The surgical tool may include a tissue cutting or bone abrading implement, or an implement such as a forceps or grasper for gripping body material. In so-called "punch" arthroscopic instruments, the surgical tool includes a hinged jaw and a stationary jaw mounted on the stationary member near its distal end. The actuating member pivots the hinged jaw, thereby closing and opening the jaws to cut tissue. Examples of these surgical instruments are described in U.S. Pat. Nos. 4,522,206, 4,662,371, both of which are assigned to the present assignee and incorporated herein by reference. In arthroscopic scissor instruments, either or both cutting jaws are hinged. A grasper typically includes jaws that lack cutting edges so as to grasp, rather than cut, body material when the jaws are closed.

Other types of surgical tools include a rotating cutting blade (examples of which are described in U.S. Pat. Nos. 4,203,444, 4,274,414, 4,834,729) or a boneabrading burr (an example of which is described in U.S. Pat. No. 4,842,578). All of these patents are assigned to the present assignee and incorporated herein by reference.

In some arthroscopic instruments the actuating member rotates within the stationary member. The outer, stationary member is sometimes curved to facilitate positioning a cutting implement against tissue to be cut without requiring that the instrument be removed from the body and reinserted through an additional puncture. In one such instrument, the portion of the actuating member disposed within the curve includes a separate flexible section made from a series of coaxial, oppositely-wound spiral layers that enables the actuating member to accept the curvature imposed by the stationary member while transmitting rotational force (i.e., torsion) applied by a driving motor to the blade.

SUMMARY OF THE INVENTION

One general aspect of this invention is a surgical instrument in which a surgical tool is carried distally of a bend region in a stationary support member by an assembly that transmits proximally applied forces through the bend region to both operate the surgical tool and selectively change the rotational orientation of the surgical tool with respect to the stationary member.

The invention allows the user to rotate the surgical tool, rather than the entire surgical instrument, to change the angle of attack of the surgical tool, despite the curvature imposed by the bend region. Because the surgical tool can be rotated to any desired angular position, the invention allows a single surgical instrument to be used to grasp or cut tissue at any angular orientation with respect to the axis of the instrument. This eliminates the need for a set of curved instruments having surgical tools located at different fixed angular positions (e.g., directed up, down, to the left, and to the right with respect to the axis of the instrument), and also allows the user to position the tool at any angular orientation (rather than at one of the restricted number of orientations that would be provided by the set of instruments). As a result, the surgical instrument need not be removed from the body and reinserted (or replaced with an instrument having a differently-oriented tool) to act on difficult to reach tissue. This greatly simplifies the surgical procedure and reduces the risk of complications to the patient.

Preferred embodiments include the following features.

The proximally applied forces are directed in different directions with respect to the axis of the instrument. More specifically, an axial force is applied to operate the tool, and a rotational force is transmitted to change the rotational orientation of the tool.

The assembly includes a movable member that rotates to change the rotational orientation of the surgical tool, and a driver member that slides axially to operate the tool. The members are disposed coaxially with each other within the stationary member. At least a portion of the movable member and the driver member is relatively flexible to allow the member to transmit the applied force through the bend region to the surgical tool.

The movable member includes a generally rigid, rotatable tube that includes a flexible region disposed within the bend region. The flexible region is relieved with a plurality of openings, such as a series of axially spaced, circumferentially extending slots. As a result, the flexible region is sufficiently pliable to accommodate itself to the curvature imposed by the bend region, but is also sufficiently torsionally stiff to efficiently transmit rotational force (i.e., torque) to the surgical tool. The length of the flexible region is selected so that adjacent rigid portions of the rotasable tube are disposed outside of the bend region (i.e., witch, in straight sections of the stationary member).

In one embodiment, the driver member is a generally rigid, slidable tube that includes a relatively flexible region disposed within the bend region. The flexible region is provided by an axially elongated opening in the walls of the tube. The elongated opening allows the slidable tube to accommodate itself to the curvature of the bend region, but is substantially noncompressible in the axial direction. As a result, the flexible region of the driver member efficiently transmits axial forces translationally through the bend region to operate the surgical tool.

The amount by which the elongated opening extends radially into the tube is a function of the degree of flexibility and axial strength desired. In one embodiment, the opening extends between 60% and 70% of the diameter of the tube. The axial extent of the opening should be sufficient so that rigid portions of the tube adjacent to the flexible region lie outside of the bend region.

The slidable tube is radially disposed within the stationary member so that the portion of the slidable tube that circumferentially bounds the elongated opening forms a leaf spring that is disposed adjacent to the portion of the bend region having a maximum radius of curvature. Alternately stated, the leaf spring is disposed opposite to the direction in which the bend region is offset from the axis. This orientation helps ensure that the leaf spring is supported as it slides axially to more efficiently operate the surgical tool. In this embodiment, the driver member is rotationally decoupled from the surgical tool to retain the desired radial orientation of the leaf spring as the tool is rotated.

The surgical tool includes, for example, a stationary jaw carried by the rotatable tube and a movable jaw that is pivoted by the axial movement of the sliding tube. The sliding tube moves distally to close the movable jaw against the stationary jaw, and is drawn proximally to open the jaws. The rotatable tube applies the rotational force to the stationary jaw, which engages the hinged jaw as it rotates to cause the tool to rotate as a unit about the axis.

The surgical tool is, for example, a cutting instrument (e.g., to provide an arthroscopic "punch" instrument), and the elements of the tool are jaws with sharp, tissue-severing edges. In this embodiment, the slidable tube includes a passage for transporting tissue fragments cut by the jaws through the instrument in response to proximally applied suction. This allows tissue fragments and irrigation fluid to be removed while the surgical instrument remains in place for further cutting. In another embodiment, the surgical instrument is a forceps or grasper, and the jaws of the surgical tool are fashioned to grip, rather than cut, tissue. Such a instrument need not include a suction passage.

The surgical instrument is a manual instrument and includes a handpiece that supports the movable member. An actuator (such as a knob) on the handpiece is linked to the movable member to allow the user to rotate the movable member (and hence the surgical tool) by turning the knob.

In another embodiment of the surgical instrument (particularly useful for forceps) the driver member is constructed to operate the surgical tool by sliding proximally away from the tool to close the jaws. In this embodiment, the driver member is a flexible cable (although the driver member may alternatively be a rigid tube with a flexible section disposed within the curved region of the outer tube). One end of the cable engages the pivotable jaw, with the other end being received by the handpiece. A trigger on the handpiece is linked to the cable to apply axial forces to the cable, and hence to the surgical tool, when the trigger is actuated. The cable is rotatably coupled to the surgical tool to rotate with the surgical tool. The proximal end of the cable is rotatably mounted within the handpiece to help prevent the cable from twisting and kinking when the user rotates the surgical tool.

The handpiece may include a pressure relief mechanism for decoupling the trigger from the slidable tube if the force applied by the user exceeds a threshold. This avoids the application of excessive axial forces to the surgical tool which could damage or destroy the tool. The pressure relief mechanism includes a spring for coupling the trigger to the slidable tube. The spring is preloaded to transmit axial forces that are below the threshold to the tube, but compresses in response to forces that exceed the threshold. Thus, if a bone fragment or other hard material becomes lodged between the jaws and the user nonetheless tries to close the jaws, the spring compresses when the threshold is reached, thereby allowing the user to continue to apply pressure to the trigger, but decoupling the excessive force from the jaws.

The stationary member need not include a bend region to take advantage of the techniques of the invention. In another aspect of the invention, an intermediate member disposed within the stationary member transmits rotational force to the surgical tool to selectively change the rotational orientation of the tool, and an inner member disposed within the intermediate member transmits axial force to the surgical tool to operate it.

In yet another aspect of the invention, the stationary member includes the bend region, and a movable member supported by the stationary member is constructed to transmit a proximally applied axial force through the bend region to operate a surgical tool disposed in a distal region of the instrument. The surgical tool need not be rotatable with respect to the stationary member.

Preferred embodiments include the following features.

The movable member slides axially within the outer member in response to the applied axial force. The movable member is a generally rigid tube that is rendered relatively flexible within the bend region by an axially elongated slot in the walls of the tube. The surgical tool includes cutting jaws that are opened and closed as the tube slides within the stationary member, and tissue fragments severed by the jaws are withdrawn through a transport passage in the tube.

Other features and advantages of the invention will become apparent from the following detailed description, and from the claims.

DESCRIPTION OF THE PREFERRED EMBODIMENTS

Structure

Figure 1:
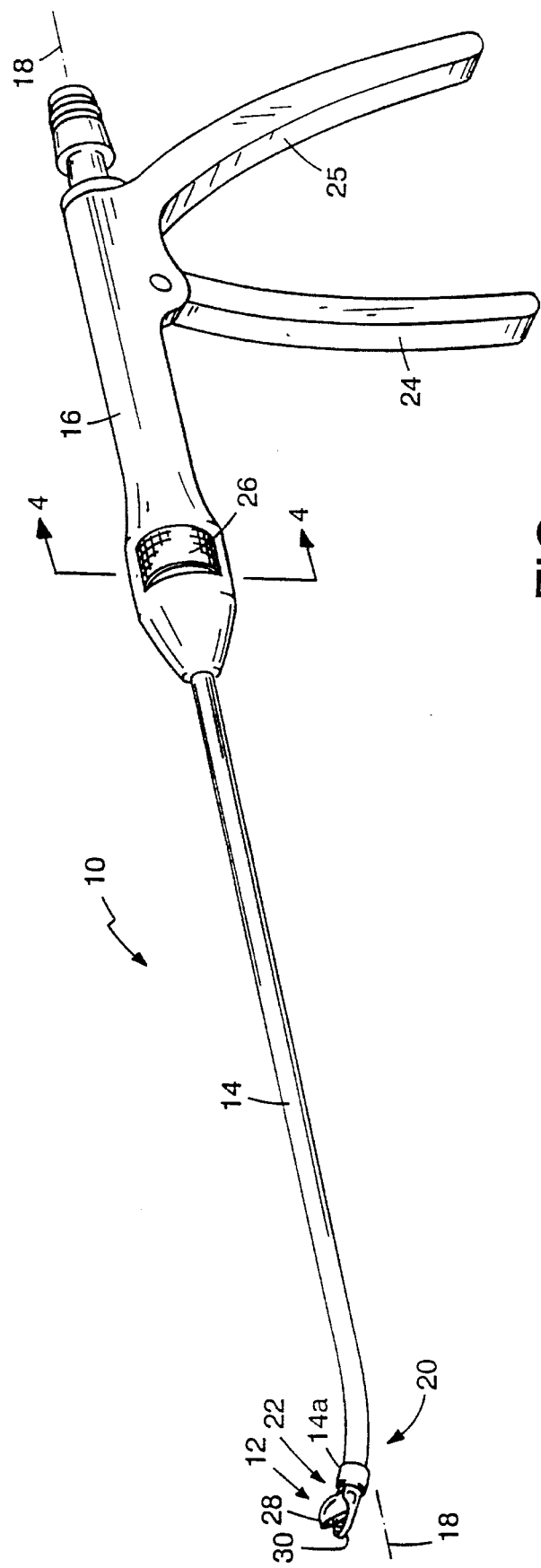
FIG. 1 is a perspective view of a surgical instrument according to ore embodiment of the invention.

Referring to FIG. 1, surgical instrument 10 is a "punch" type arthroscopic instrument that includes a surgical tool 12 disposed at the distal end of a stationary tube 14, the proximal end of which is mounted on a handpiece 16. Stationary tube 14 lies generally along a longitudinal axis 18, but includes a bend region 20 disposed slightly proximally of its distal end. Bend region 20 serves to angularly offset the distal end of tube 14, and hence surgical tool 12, from axis 18. Surgical tool 12 is supported for operation and rotation with respect to stationary tube 14 by a mounting assembly 22 (described in detail below), which protrudes through the open distal end 14a of stationary tube 14 (only the distal portion of mounting assembly 22 is shown in FIG. 1). Mounting assembly 22 extends proximally within stationary tube 14, through bend region 20, and terminates within handpiece 16.

The construction and operation of mounting assembly 22 is discussed in detail below. Suffice it here to say that mounting assembly 22 is constructed to transmit forces applied at handpiece 16 through bend region 20 to allow the user to operate surgical tool 12 and selectively change the rotational orientation of tool 12 with respect to stationary tube 14 and about axis 18 without having to rotate handpiece 16. The user (e.g., a surgeon) operates surgical tool 12 by squeezing and releasing a spring-loaded trigger 24, thereby applying axial forces to mounting assembly 22, which transmits these forces translationally through bend region 20 to open and close a pivotable jaw 28 with respect to a stationary jaw 30 of surgical tool 12. The user adjusts the rotational orientation of surgical tool 12 by turning a knob 26 mounted on handpiece 16; mounting assembly 22 transmits this rotational force through bend region 20 to rotate jaws 28, 30 while tube 14 remains stationary.

Figure 2:
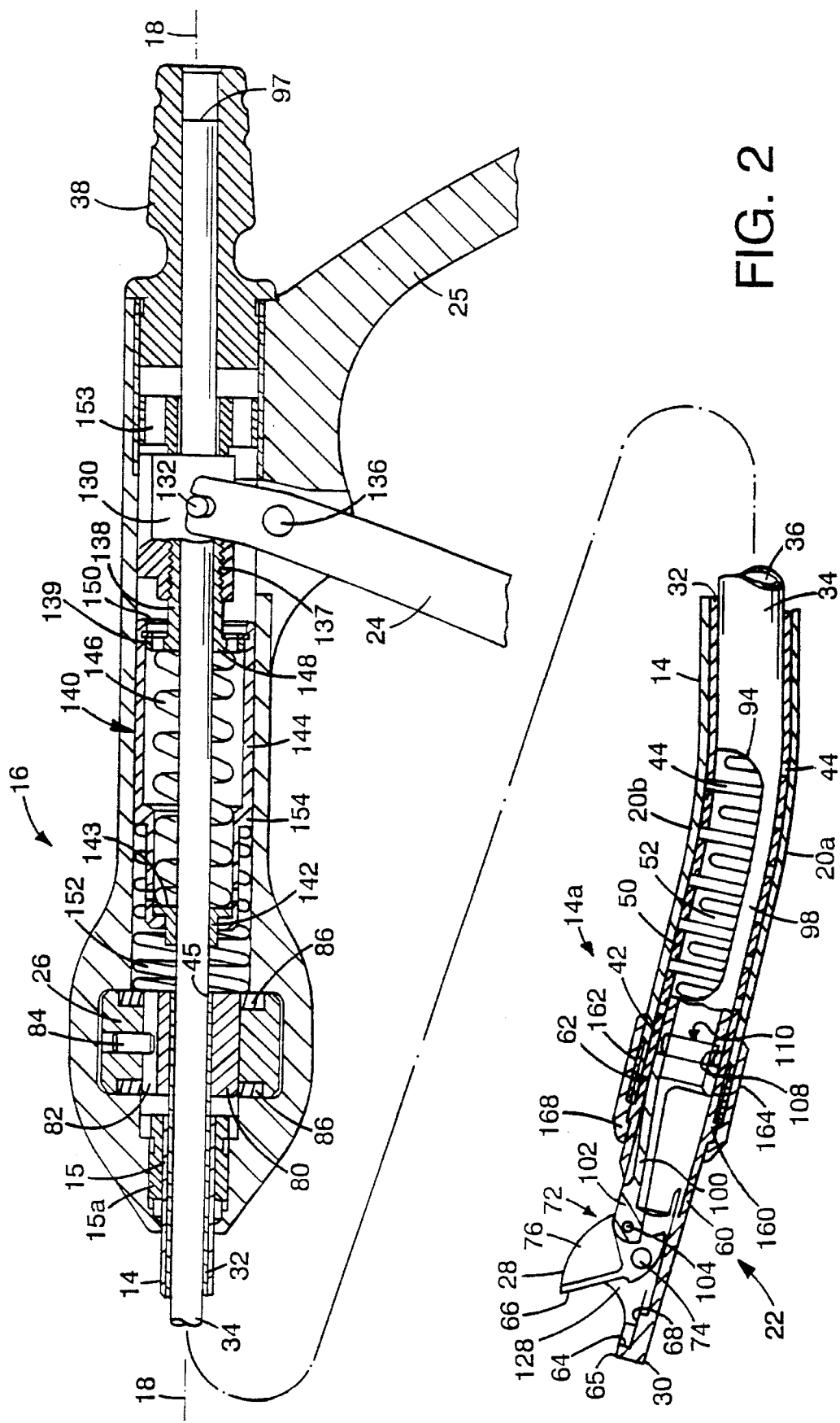
FIG. 2 is a partial cross-sectional view of portions of the surgical instrument of FIG. 1.

Referring also to FIG. 2, mounting assembly 22 includes a pair of coaxial tubes 32, 34 disposed within outer stationary tube 14. Tube 32 is disposed radially between outer, stationary tube 14 and innermost tube 34, and carries surgical tool 12 in a manner described in detail below. (For clarity, intermediate tube 32 and stationary tube 14 are shown in cross-section, but inner tube 34 is not.) Intermediate tube 32 responds to the rotation of knob 26 (FIG. 1) by revolving within tube 14 to change the rotational orientation of surgical tool 12. Inner tube 34 serves as a driver for surgical tool 12 and slides axially (i.e., translationally) within intermediate tube 34 in response to the actuation of handpiece trigger 24 to operate surgical tool 12. The hollow interior of tube 34 provides a passage 36 for the removal of body material (e.g., tissue fragments) cut by tool 12 and irrigation fluid in response to suction applied to a fitting 38 on the proximal end of handpiece 16.

To enable tubes 32, 34 to apply sufficient rotational and axial forces to surgical tool 12, tubes 32, 34 are generally rigid members (made from a metal such as stainless steel). The portions of tubes 32, 34 that lie within bend region 20 are flexible to allow tubes 32, 34 to both accommodate themselves to the curvature imposed by bend region 20 without becoming unduly stressed, and to transmit the applied rotational and axial forces through (i.e., beyond) bend region 20 to surgical tool 12.

Figure 3:
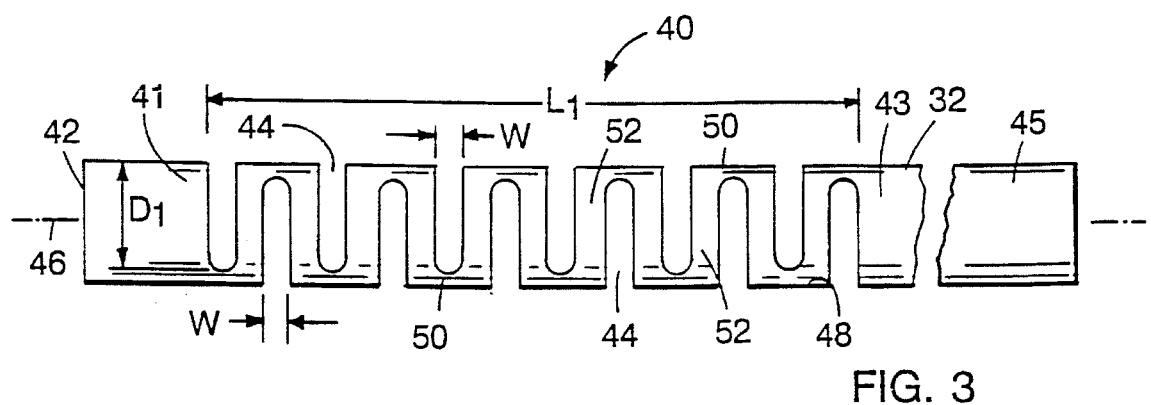
FIG. 3 shows details of one of the members of the surgical instrument of FIG. 1.

Referring also to FIG. 3, intermediate tube 32 includes a flexible region 40 disposed slightly proximally of distal end 42. Flexible region 40 is relieved with an axially extending series of circumferential slots 44 disposed in the walls 48 of tube 32 and is continuous with the rigid regions 41, 43 disposed adjacent to the distal and proximal ends of flexible region 40. (Slotting a rotatable tube for flexibility within a stationary outer tube is described in a copending application entitled "Surgical Instruments," Ser. No. 07/634,599, filed on Dec. 27, 1990, now U.S. Pat. 5,152,744, which is assigned to the present assignee and incorporated herein by reference.) Slots 44 are generally perpendicular to the longitudinal axis 46 of tube 232 and are arranged in a symmetrical pattern along the length $L_1$ of flexible region 40 to provide uniform flexibility and avoid any substantial deviations in flexibility as tube 32 is rotated within stationary tube 14. This minimizes torsional stresses on tube 32 and helps increase the operating life of surgical instrument 10.

Slots 44 are disposed parallel to each other (vertically in FIG. 3) along length $L_1$. Adjacent slots 44 extend into tube 32 from opposite directions (e.g., from above and below tube 32 in FIG. 3) and are circumferentially offset from each other by 180°. The number of slots 44, their dimensions (i.e., their width W and depth $D_1$), and the spacing between adjacent slots are a function of the desired degree of flexibility. In this example, the width W of each slot 44 and the spacing between slots 44 each are 0.20 inches.

A tab 50 bounds each slot 44 circumferentially, and adjacent tabs 50 are interconnected by annular rings 52, which provide the spacing between adjacent slots 44. The interconnected series of rings 52 and tabs 50 provide a series of interconnected, integrally formed "U" shaped leaf springs along the length $L_1$ of flexible region that yield uniform flexibility and efficiently transmit torque (i.e., rotational force) applied at a proximal end of tube 32 to distal end 42 through the curvature imposed by bend region 20 (FIG. 1). The depth $D_1$ of slots 44 (i.e., the amount by which slots 44 extend radially into tube 32) is a function of the desired torsional strength of flexible region 40. In this example, depth $D_1$ is between 60% and 75% of the outer diameter (0.130 inches) of tube 32.

The length $L_1$ of flexible region 40 is a function of the length of bend region 20. Flexible region 40 should be sufficiently long (e.g. 0.42 inches) so as to span the entire length of bend region 20 with one or two slots 44 disposed on each side of bend region 20. Adjacent rigid portions 41, 43 of tube 32 lie in straight regions of stationary tube 14. This allows flexible region 40 to make a smooth transition between the straight regions of stationary tube 14 and bend region 20, thereby reducing stresses imposed by the curved inner walls of bend region on walls 48 of intermediate tube 32.

Flexible region 40 can be formed by any suitable method. Examples include wire EDM (electric discharge machining) and sawing. Both are described in the aforementioned U.S. patent application Ser. No. 07/634,599.

As shown in FIG. 2, distal end 42 of intermediate tube 32 is rigidly attached (such as by welding) to a stainless steel tubular extension 60 at a seam 62. (Tubular extension 60 is constructed similarly as that shown in aforementioned U.S. Pat. No. 4,662,371, hereinafter, "the '371 patent".) The distal end of tubular extension 60 forms jaw 30 of surgical tool 12, the inner cutting edges 64 of which are sized and configured to receive outer cutting edges 66 of jaw 28 in close sealing relationship to sever body material. The top surface 65 of jaw 30 is burnished as described in the '371 patent to ensure close tolerance between jaws 28, 30 for clean cutting. The floor 68 of jaw 30 is relieved in a pair of steps as floor 68 extends proximally toward tissue transport passage 36 to facilitate the removal of severed tissue fragments into passage 36.

The underside of extension 60 is closed, while the upper side of tubular extension 60 includes an opening 72 to accommodate pivotal jaw 28. Jaw 28 is pivotally mounted to tubular extension 60 by a pin 74. Jaw 28 is generally hood-shaped, shaped, with the upper portion of hood 76 extending through opening 72; the lower portion of hood 76 terminates in cutting edge 66. Jaw 28 is connected to inner member 34 in a manner described in detail below.

Intermediate tube 32 extends proximally through stationary tube 14 to handpiece 16. The proximal end 45 of intermediate tube 32 extends proximally of the proximal end 15 of stationary tube 14 in handpiece 16. (Proximal end 15 of stationary tube is rigidly mounted by fitting 15a on handpiece 16.) Proximal end 45 of intermediate tube 32 is secured (such as by welding) to a round sleeve 80 which in turn is engaged by knob 26.

Figure 4:
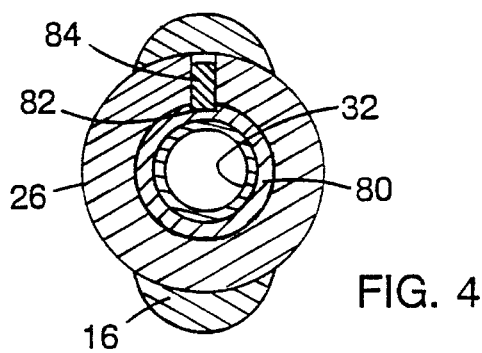
FIG. 4 is a cross-section, taken along line 4—4 of FIG. 1, of a portion of the mechanism for rotating the surgical tool.

Referring also to FIG. 4 (which for clarity does not show inner tube 34), sleeve 80 includes a slot 82 which receives a pin 84 that protrudes inwardly from knob 26 (more than one pin-slot pair may be used). Pin 84 is press fit within knob 26. Thus, as the user rotates knob 26 with respect to handpiece 16, the rotation is transferred to sleeve 80 (and hence to intermediate tube 32) by the engagement of pin 84 against the walls of slot 82. Knob 26 projects from the sides of handpiece 16 for easy accessibility by fingers of the same hand that is used to operate trigger 24. Because the user is more likely to engage knob 26 from the side, knob 26 does not protrude from the upper or lower surfaces of handpiece 16 (but, of course, such a modification can easily be made).

A pair of thrust washers 86 are disposed between radial surfaces of knob 26 and handpiece 16 to reduce metal-to-metal friction. Sufficient resistance to rotation is provided by this configuration to maintain knob 26 (and hence surgical tool 12) in the rotational position set by the user and avoid accidental or unwanted rotation. The outer surface of knob 26 is knurled (FIG. 1) to allow the user to easily engage and turn knob 26.

Figure 5:
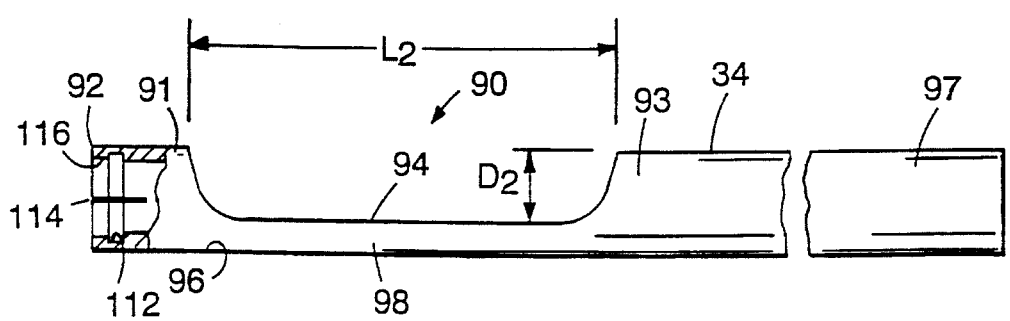
FIG. 5 shows details of another one of the members of the instrument of FIG. 1.

Details of inner tube 34 are shown in FIGS. 2 and 5. As explained in detail below, inner tube 34 slides axially within intermediate tube 32 in response to the actuation of trigger 24 to operate surgical tool 12 by opening and closing jaws 28, 30. Inner tube 34 includes a flexible region 90 disposed slightly proximally of the distal end 92 of inner tube 34 and positioned to lie within bend region 20 of stationary tube 14. Flexible region 90 is integrally formed to be continuous with the adjacently disposed rigid portions 91, 93 of tube 32 and is relieved with a single, axially elongated slot 94 disposed in tube walls 96. The material 98 that circumferentially bounds slot 94 forms an axially extending leaf spring that interconnects rigid regions 91, 93.

Leaf spring 98 is sufficiently flexible to accommodate itself to the curvature imposed by bend region 20 (FIG. 2). At the same time, leaf spring 98 is sufficiently rigid in the axial direction to transmit the axial force applied by trigger 24 through bend region 20 to operate surgical tool 12. The flexibility and axial stiffness of region 90 are, of course, a function of the axial extent ($L_2$) and the depth ($D_2$) of slot 94. Flexible region 90 should be longer than bend region 20 by at least the amount of actuation of inner tube 34 so that adjacent rigid portions 91, 93 of inner tube 34 do not enter bend region 20 during operation. Here, $L_2$ is 0.47 inches long.

Slot 94 should be formed to a depth $D_2$ sufficient to allow flexible region 90 to accept the curvature imposed by bend region 20 without becoming overly stressed; yet $D_2$ should not be so large as to weaken leaf spring 98 to the point where flexible region 90 cannot deliver the axial force required to cause surgical tool 12 to cut body material. In this example, depth $D_2$ is between 60% and 75% of the outer diameter (e.g., 0.110 inches) of inner tube 34. Slot 94 is formed by any suitable technique, such as EDM, sawing, etc.

Inner tube 34 is radially oriented within intermediate tube 32 and stationary tube 14 so that leaf spring 98 is positioned opposite to the direction of curvature of bend region 20. Leaf spring 98 thus is disposed adjacent to the portion of bend region 20 that has the greatest radius of curvature. For example, in the arrangement shown in FIG. 2 in which bend region 20 curves upwardly with respect to handpiece 16 and axis 18, the lower portion 20a of bend region 20 has a greater radius of curvature than upper portion 20b, and inner tube 34 is oriented so that leaf spring 98 faces lower portion 20a. As a result, when inner tube 34 slides axially within intermediate tube 34 and stationary tube 14 toward surgical tool 12, leaf spring 98 bears against the interior surface of intermediate tube 32. Thus, leaf spring 98 gains support from intermediate tube 32, thereby reducing the risk that leaf spring 98 will buckle or break when operating surgical tool 12. (This risk would be greatest if inner tube 34 were to be oriented with leaf spring 98 facing upper portion 20b of bend region 20. In this case, leaf spring 98 would actually be urged away from the interior surface of intermediate tube 32 as inner tube 34 slides axially toward surgical tool, and would thus receive no support from tube 32.)

As shown in FIG. 2, inner tube 32 drives jaw 28 of surgical tool 12 through a tang 100. The distal end 102 of tang 100 is pivotally attached to jaw 28 with pin 104. The proximal end of tang 100 is tubular and engages distal end 92 of inner tube 34 through a rotational slip joint 110. Slip joint 110 allows inner tube 34 to remain rotationally fixed (and thus maintain the above-described radial positioning of leaf spring 98 within bend region 20) when the user changes the rotational orientation of surgical tool 12.

Slip joint 110 is formed by the engagement of an enlarged ridge 108 at the proximal tip of tang 100 (FIG. 2) within a corresponding circular slot 112 in walls 96 of distal end 92 of inner tube 34 (FIG. 5). Distal end 92 includes a series of (such as four) circumferentially spaced, narrow notches 114 (shown in FIG. 5 only) that allow distal end 92 to be resiliently expanded over the proximal end of tang 100 during assembly. With slip joint 110 assembled, a ridge 116 on distal end 92 fits within an annular cavity (not numbered) in the proximal end of tang 100 to help prevent axial play between inner tube 34 and tang 100. Ridge 116 is slightly thinner than walls 96 (e.g., by 0.005 inches) for ease of assembly.

Figure 6:
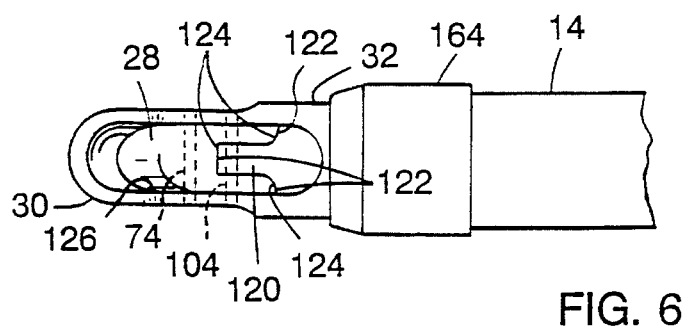
FIG. 6 is a top view of the surgical tool of the instrument of FIG. 1.

Referring also to FIG. 6, the distal end of tang 100 includes an extension 120 that receives pin 104. Extension 120 includes a set of forward bearing surfaces 122 that oppose and engage a corresponding set of rearward-facing bearing surfaces 124 on the proximal end of jaw 28. As a result, the translational force transmitted by inner tube 34 is applied by tang 100 to jaw 28 by the engagement of bearing surfaces 122, 124, rather than simply through pin 104. This reduces the stresses applied to pin 104 and the concomitant risk of breakage.

As discussed above, jaw 28 rests within an opening 72 in tubular extension 60 (FIG. 2). A close fit is provided between the longitudinally extending sides 126 of jaw 28 and the sides 128 of opening 72. This reduces the stresses imposed on pins 74, 104 when surgical tool 12 is rotated about axis 18, because as tubular extension 60 and lower jaw 30 are rotated by intermediate tube 32, the rotational forces are applied against jaw 28 through the engagement of sides 126, 128 rather than simply through pins 74, 104.

Inner tube 34 extends completely through intermediate tube 32, with the proximal end 97 of tube 34 terminating within suction fitting 38 of handpiece 16. Slightly distally of proximal end 97, inner tube 34 passes through a bracket 130, the sides of which are equipped with pins 132 for engaging a corresponding pair of slots on trigger 24. Trigger 24 is pivotally mounted to handpiece by pin 136. Bracket 130 is axially secured to a fitting 138 disposed around inner tube 34. Fitting 138 snugly engages inner tube 34 but is not axially secured to inner tube 34 for reasons that shall become apparent. Bracket 130 is threaded 137 onto fitting 138 to allow their relative axial positions to be varied to adjust the position of trigger 24 to remove any play in the movement of trigger 24 that does not operate tool 12.

A pressure relief assembly 140 receives an enlarged end 139 of fitting 138. The distal end of pressure relief assembly 140 is rigidly secured in an axially fixed position to inner tube 34 by fitting 142. Pressure relief assembly 140 includes a hollow housing 144 through which inner tube 34 passes and that also contains a relief spring 146. Spring 146 is highly preloaded (e.g., to about 130 lbs.) for purposes to be discussed, and is compressed between a radial surface 143 of fitting 142 and a similar radial surface 148 of the enlarged end 139 of fitting 138. A snap ring 150 is secured on the proximal end of housing 144 to capture fitting 138 and spring 146 within housing 144. A return spring 152 is compressed between the proximal radial surface of knob 26 and a shoulder 154 of housing 144.

Assembly

Surgical instrument 10 is assembled as follows. First, intermediate tube 32 and inner tube 34 are fabricated in the manner discussed above. Tubular extension 60 is welded to distal end 42 of intermediate tube 32, and tang 100 is attached to distal end 92 of inner tube 34 at slip joint 110. Notches 114 allow distal end 92 to resiliently expand as tang 100 is inserted, and then retract to securely retain ridge 108 within slot 112. Intermediate tube 32 is inserted through the distal end of outer tube 14 (before tube 14 is curved to form bend region 20), and sleeve 80 is then attached to the proximal end of tube 32 by brazing or welding. Next, inner tube 34 is inserted proximally through housing 144 and intermediate tube 32, and hinged jaw 28 is attached to extension 60 and tang 100 with pins 74, 104, respectively. Then, pressure relief spring 146 is inserted into housing 144 around inner tube 34, followed by fitting 138. Pressure relief spring 146 is compressed and retained within housing 144 by installing snap ring 150.

Tubular extension 60 includes a raised circular flange 160 (FIG. 2) that abuts distal end 14a of stationary tube 14 when tubes 32, 34 are fully inserted. Flange 160 has the same outer diameter (e.g. 0.165 inches) as stationary tube 14. Tube 14 includes a set of exterior threads 162 that extend a short distance proximally of distal end 14a to receive corresponding interior threads of a collar 164 that includes an annular recess for receiving flange 160. With collar 164 installed on stationary tube 14, flange 160 is captured between a circular shoulder 168 on collar 164 and distal end 14a of tube 14, which form a slip joint that allows tubular extension 60 to rotate within the recess.

Assembly is completed by securing the proximal ends of intermediate tube 32 and inner tube 34 within handpiece 16 and assembling handpiece 16. Bend region 20 is then formed in outer tube 14 by any suitable technique. Care should be taken that tube 14 is not creased during bending. Bend region 20 is located about 0.70 inches proximally of the distal tip of instrument 10, but of course other positions are possible. Bend region 20 is configured to offset surgical tool 12 from axis by any suitable amount (for example, 15°, 30°, 45°, etc.).

Operation

Figure 7:
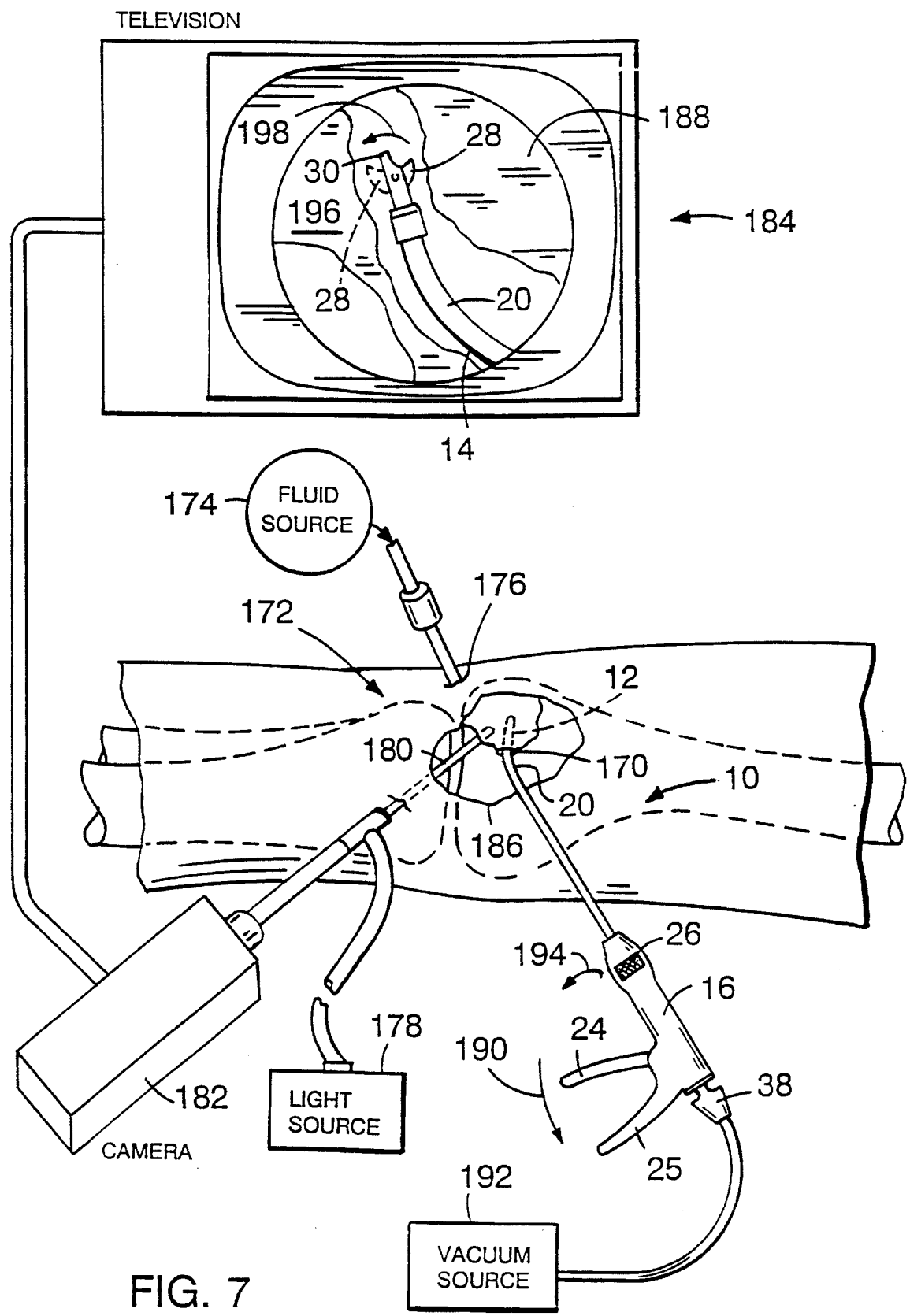
FIG. 7 shows the surgical instrument of FIG. 1 in use.

Referring to FIG. 7, in operation, surgical. instrument 10 is inserted through a puncture wound 170 into a joint space 172 (such as a knee joint) in the body. Irrigation fluid is introduced from a source 174 through a second puncture opening 176. The surgical site 186 within joint space 172 is illuminated with light supplied by a source 178 through a fibre optic coupler 180, which also transmits an image of the surgical site to camera 182. The image is also displayed by a television 184 to enable the surgeon to clearly visualize the procedure.

The surgeon manipulates handpiece 16 (e.g. up or down, to the left or to the right) to position surgical tool 212 adjacent to body material (such as cartilage or synovial tissue) to be cut. For example, surgical instrument 10 is manipulated to place surgical tool 12 at the underside of tissue 188. The curvature provided by bend region 20 facilitates placing surgical tool 12 against hard-to-reach tissue without requiring surgical instrument 10 to be removed from joint space 172 and reinserted through another puncture wound. As described in aforementioned U.S. application Ser. No. 07/634,599, this helps minimize trauma and reduce the risk of infection or other complications from the surgical procedure.

The surgeon causes surgical tool 12 to cut tissue 188 by squeezing trigger 24 toward handle 25 in the direction of arrow 190 (for example, by allowing handle 25 to rest against the palm of the hand and using the middle fingers of the hand to operate trigger 24). As shown in FIG. 2, trigger 24 urges bracket 130 forward, applying axial force against pressure relief spring 146. The large preloading of spring 146 prevents spring 146 from compressing unless the user applies excessive pressure to trigger 24 (this situation is discussed below). Thus, the axial force is applied against fitting 142, causing inner tube 34, housing 144, and spring 146 to slide as a unit axially with respect to intermediate tube 32 (which is held in an axially fixed position by collar 162). Note that inner tube 34 remains within vacuum fitting 38 as it slides within handpiece 16.

As inner tube 34 slides distally, tang 100 is urged forward, pivoting jaw 28 about pin 74 and operating surgical tool 12 by closing jaw 28 against jaw 30. Surgical tool 12 is initially rotationally oriented so that jaw 28 opens upwardly (FIG. 7) to progressively cut tissue 188. Flexible region 90 slides smoothly within intermediate tube 32 through bend region with leaf spring 98 bearing against and being supported by intermediate tube 32. As a result, flexible region 90 efficiently transmits the applied axial force through bend region 20 to surgical tool 12. The flexibility of region 90 reduces stresses that bend region 20 imposes on inner tube 34, thereby significantly reducing the risk of inner tube 34 breaking in response to the applied force, even over many cycles of operation.

The operating life of surgical instrument 10 is further enhanced by the arrangement of bearing surfaces 122, 124 on tang 100 and jaw 28. Because tang 100 applies the translational forces to jaw 28 through bearing surfaces 122, 124, rather than simply against pin 104, the stresses on pin 104 are dramatically decreased. This minimizes the risk of pin 104 snapping during use, particularly when the user applies large amounts of cutting pressure to trigger 24.

Jaws 28, 30 are opened simply by releasing the pressure on trigger 25. Return spring 152, which is axially compressed as inner tube 34 and housing 144 slide axially within handpiece 16, urges pressure relief assembly 140, and hence inner tube 34, to slide proximally as trigger 24 is released. The sliding inner tube 34 pulls tang 100 proximally as well, thereby pivoting jaw 28 away from jaw 30 about pin 74. Bracket 130 engages a backstop 153 when trigger 24 is fully open to limit the travel of trigger 24 and the amount that jaw 28 opens.

A vacuum source 192 connected to fitting 38 of handpiece 16 applies suction through tissue transport passage 36 of inner tube 34, which serves to draw body material 188 between jaws 28, 30 for cutting. The vacuum also draws irrigation fluid and fragments of body material 188 cut by the sharp edges 64, 66 of jaws 28, 30 through a tissue transmitting throat between jaw 28 and underside 70 of tubular extension 60 (which are configured to provide such a throat, as described in the aforementioned U.S. Pat. No. 4,662,371), through tang 100, and into tissue transport passage 36. As a result, the fragments are withdrawn from surgical site 186 while instrument 10 remains in place for further cutting.

When the surgeon wishes to cut other body material, such as tissue 196 located below surgical tool 12, he or she rotates knob 26, for example, in the direction of arrow 194. The applied rotational force is transferred to intermediate tube 32 by the engagement of pin 84 with sleeve 80 (FIG. 4), thereby causing intermediate tube 32 to rotate with respect to outer tube 14 and inner tube 34. Flexible region 40 transmits the applied rotational force through bend region 20 to surgical tool 12, specifically, to jaw 30 via tubular extension 60. Jaw 30 and tubular extension 60 thus rotate as a unit within the slip joint provided by collar 160 in the direction of arrow 198. As jaw 30 rotates, side surfaces 128 of extension 60 bear against side surfaces 126 of jaw 28, thereby forcing jaw 28 to rotate without placing undue stress on pin 74.

The surgeon continues to rotate knob 26 until surgical tool 12 has reached the desired rotational orientation with respect to axis 18 (for example, with jaw 28 in the position shown in phantom in FIG. 7, which for clarity does not shown the corresponding position of jaw 30). If desired, the surgeon can continue the rotation a full 360° in the direction of arrow 198; alternatively, the surgeon can reverse the direction of rotation simply by turning knob 26 in the opposite direction. As a result, the surgeon can freely rotate surgical tool 12 without twisting handpiece 16 at all (for example, by using the forefinger of the hand that holds handpiece 16 to turn knob 26). This allows handpiece 16 to be maintained in a comfortable operating position (such as that shown in FIG. 7) at all times. Bend region 20 and outer tube 14 remain rotationally fixed, thereby eliminating the need to reposition outer tube 14 as surgical tool 12 rotates.

Slip joint 110 allows intermediate tube 32 to rotate independently of inner tube 34 by permitting tang 100 to rotate within slot 112 on the distal end of tube 34. Accordingly, inner tube 34 remains rotationally fixed in the position shown in FIG. 2. This maintains leaf spring 98 in position to bear against intermediate tube 32 as inner tube 34 slides axially in response to trigger 24.

The amount of force applied to trigger 24 by the surgeon to cut body material with surgical is a function of the strength of the material being cut. Relatively soft material (such as synovium) will require less applied force to be cut than will harder material (such as cartilage). Occasionally, hard body material that cannot readily be cut by surgical tool 12 (such as a bone fragment) may become lodged between jaws 28, 30. The surgeon may attempt to cut the fragment by applying still greater force to trigger 24, but if the fragment is sufficiently hard, it may break one or both of jaws 28, 30 (which may then become lodged in surgical site 186) if sufficient force is applied. Pressure relief assembly 140 avoids this undesirable result by limiting the amount of force that the surgeon is permitted to apply to surgical tool 12.

As discussed above, pressure relief spring 146 is preloaded to, for example, 130 lbs. and thus, under normal circumstances, is not axially compressed as the surgeon squeezes trigger 24. The preloading is overcome, however, and spring 146 is axially compressed if the force applied to trigger 24 exceeds a threshold that should be applied to tool 12 (for example, if a bone fragment or the like prevents jaws 28, 30 from closing and the surgeon applies excessive force to trigger 24). As spring 146 compresses, fitting 138 slides over inner tube 34 within pressure relief assembly housing 144, thereby decoupling trigger 24 from inner tube 34 and preventing the axial travel of trigger 24 (in the direction of arrow 190) from being transferred to inner tube 34. As a result, the excessive force is limited by the compression of spring 146 rather than being applied to surgical tool 12, even if the surgeon squeezes trigger 24 to its fully closed position.

Other Embodiments

Other embodiments are within the scope of the following claims.

For example, although surgical instrument 10 is shown with bend region 20 oriented upwardly with respect to axis 18 and handpiece 16, it is readily apparent that other orientations (e.g., downwardly, to the right or left, or anywhere in between these directions) are possible. Indeed, a set of surgical instruments may be provided, each with a different bend region 20 orientation, to give the user maximum flexibility in determining the optimum bend configuration for a given surgical procedure. Other amounts of curvature can be provided.

Moreover, either or both of tubes 32, 34 may be disposed outside of stationary tube 14.

Other surgical tools, such as scissors or the tools described in one or more of the aforementioned patents, can be used. The surgical instrument can be constructed to perform procedures other than arthroscopy (such as laparoscopy). The surgical instrument may alternatively be motor driven. Pressure relief spring 146 may be preloaded to a greater or lesser extent than 130 lbs., if desired.

Flexible regions 40, 90 may be relieved in other ways. For example, slots 44 of flexible region 40 may be arranged in other patterns (such as that shown in FIG. 3 application Ser. No. 07/634,599), or round holes may alternatively be employed. Flexible region 90 may alternatively be provided with a series of slots having the same angular orientation or an elastic section of tube 34.

One or both of flexible regions 40, 90 may be wrapped with material such as plastic to improve vacuum efficiency or help avoid tissue fragments becoming lodged on the edges of the openings. Any suitable material that does not unduly impair flexibility may be used. For example, a thin flexible tube may be shrink-fitted over flexible region 90 to enclose slot 94. And (as described in the aforementioned application Ser. No. 07/634,599) pliable material such as rubber may be inserted in slots 44 of flexible region 40.

Tubes 32, 34 need not be generally rigid metal members with flexible regions. Either tube 32, 34 may be flexible along its entire length so long as the tube is sufficiently stiff to transmit the forces applied to it (i.e., rotational and axial, respectively) to surgical tool 12. For example, tubes 32, 34 may comprise a nonmetal such as plastic, as shown in copending application Ser. No. 07/600,531, filed on Oct. 19, 1990, which is assigned to the present assignee and incorporated herein by reference.

The invention may also be used with so-called "grasper" surgical instruments that grip, rather than cut, body material.

Figure 8:
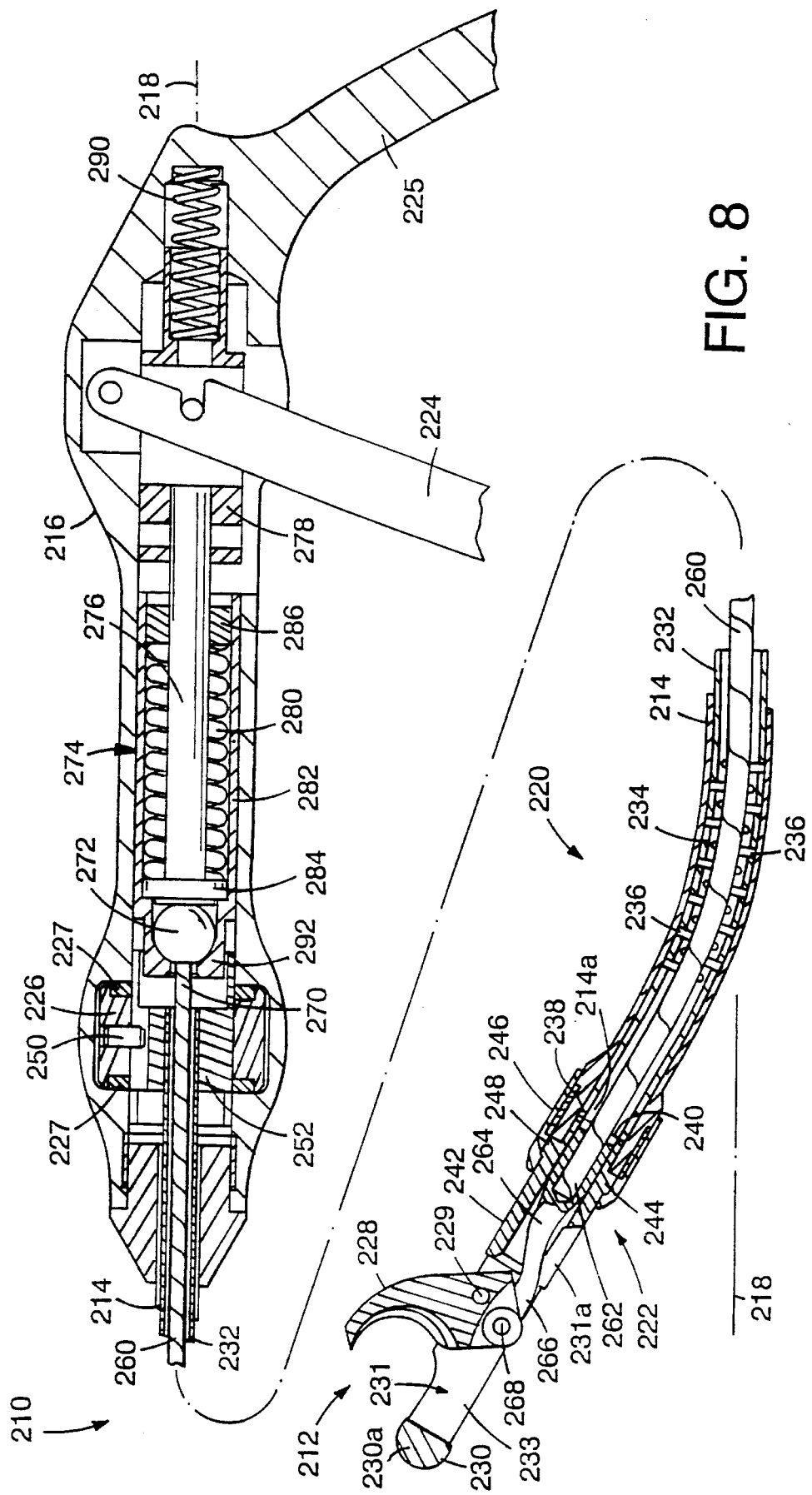
FIG. 8 is a partial cross-sectional view of portions of a surgical instrument according to another embodiment of the invention.

Referring to FIG. 8, surgical instrument 210 is a so-called "basket forceps" arthroscopic surgical instrument, the surgical tool 212 of which configured to grip, hold, and cut tissue or other body material during operation. Surgical instrument 210 includes a stationary outer tube 214 that has an open distal end 214a through which surgical tool 212 protrudes, and that terminates proximally in a handpiece 216. Outer tube 214 is generally disposed along a longitudinal axis 218, but includes a bend region 220 disposed slightly proximally of distal end 214a (e.g., by one inch).

Surgical tool 212 is supported within outer tube 214 by mounting assembly 222, which is constructed to both operate tool 212 (in response to the actuation of trigger and handle assembly 224,225 on handpiece 216) and rotate surgical tool 212 with respect to axis 218 (in response to the rotation of a knob 226 on handpiece 216).

Mounting assembly 222 includes a rotatable intermediate tube 232 that carries a jaw 230 of surgical tool 212. Intermediate tube 232 is a generally rigid member with a flexible region 234 disposed within bend region 220. Flexible region 234 is relieved with an axially extending series of slots 236 like those of tube 32 (FIG. 3). Accordingly, flexible region 234 both accommodates itself to the curvature imposed by bend region 220 and transmits rotational forces applied by knob 226 through bend region 220 to surgical tool 212.

The distal end 238 of intermediate tube 232 is welded at seam 240 to a proximal extension 242 of jaw 230. Proximal extension 242 includes a raised circular flange 244 that abuts distal end 214a of outer tube 214 when mounting assembly is fully installed in tube 214. A collar 246, which includes a recess 248 that receives flange 244, threadably engages distal end 214a to secure jaw 230 and intermediate tube 232 in a fixed axial position with respect to outer tube 214 while permitting them to rotate with respect to axis 218. The outer diameter of distal end 214a is somewhat enlarged with respect to that of the remainder of tube 214 for this purpose. An opening 231 is disposed completely through jaw 230 between its upper and lower axial surfaces to accommodate a movable jaw 228, which is pivotally mounted to jaw 230 in a manner described below. The distal end 230a of jaw 230 is rounded to reduce the risk of tissue damage.

The proximal end of intermediate tube 232 is secured to knob 226 in the same manner as discussed above for surgical instrument 10. Thus, a pin 250 in knob 226 engages a slotted sleeve 252 to couple rotational force from knob 226 to intermediate tube 232, and hence to surgical tool 212.

Intermediate tube 232 surrounds an inner member 260, which is a flexible, braided metal wire actuated by trigger 224 to slide within intermediate tube 232 and transmit axial forces through bend region 220 to drive surgical tool 212. (For clarity, inner member 260 is not shown in cross-section.) The distal end 262 of inner member 260 is connected to movable jaw 228 by an actuator 264.

Jaw 228 is pivotally mounted by pin 229 to jaw 230 within opening 231. The distal end 266 of actuator 264 engages jaw 228 at a pin 268 disposed below pin 229. Actuator 264 curves upwardly in somewhat of an "S" shape as it extends proximally to receive distal end 262 of inner member 260, which is brazed within a bore in actuator 264. The end of actuator 264 that receives inner member 260 has a round cross section and is nearly as large as the inner diameter of intermediate member 232 so as to move smoothly as inner member 260 slides. Distal end 266 of actuator 264 is flattened to fit between the shoulders of jaw 228 (see FIG. 6).

Inner member 260 extends proximally through intermediate tube 232 to handpiece 216. The proximal end 270 of inner member 260 is rigidly attached to a ball 272 that in turn is disposed for rotation within a pressure relief assembly 274. A plunger 276 connects pressure relief assembly 274 to trigger 224 via a bracket assembly 278 similar to that discussed above for surgical instrument 10. A pressure relief spring 280 disposed with plunger 276 in a housing 282 of assembly 274 is preloaded (e.g., at 25 lbs. to 30 lbs.) to urge an enlarged head 284 of plunger 276 away from a proximal wall 286 of housing 282. A return spring 290 engages bracket 224 to bias trigger 224 in the open position with respect to handle 225.

The operation of surgical instrument 210 is similar to that of surgical instrument 10. The surgeon operates surgical tool 12 to grasp body material between jaws 228, 230 by squeezing trigger 224 toward handle 225. This pulls plunger 276 proximally. Unless excessive force is applied (as described below), plunger 276 does not compress spring 280, and thus pressure relief assembly 274 slides proximally as a unit, thereby pulling inner member 260 proximally (by the engagement of ball 272 with the curved forward wall 292 of housing 282). The sliding inner member 260 pulls jaw 228 closed against jaw 230 by pivoting jaw 228 about pin 229. An axial extension 231a of opening 231 receives actuator 264 to allow jaw 228 to freely close. Jaw 228 is returned to the open position simply by releasing handle 224, which allows spring 290 to expand, thereby causing inner member 260 to slide distally and pivot jaw 228 upwardly.

Inner member 260 has a high degree of axial strength to allow the surgeon to apply firm grasping pressure to surgical tool 212 and to open jaw 228 without buckling. Yet, inner member is sufficiently flexible to transmit the applied translational force to jaw 228 through bend region 220 without becoming overstressed.

Surgical tool 212 is rotated with respect to longitudinal axis 218 by turning knob 226 in the same direction in which tool 212 is to rotate. As with surgical instrument 10, knob 26 is knurled for ease of use, and thrust washers 227 help maintain knob 226 in the rotational orientation set by the surgeon. Flexible intermediate member 232 efficiently transmits the applied rotational force through bend region 220 to jaw 230. The slip joint provided between jaw extension 242 and collar 246 allows jaw 230 to freely rotate within recess 248, thereby changing the rotational orientation of tool 212 with respect to axis 218. The sides 233 of opening 231 engage the axially extending side surfaces (not numbered) of jaw 228 to rotate jaw 228 together with jaw 230 without imposing large stresses on pins 229, 268.

The rotation of jaws 228, 230 also causes actuator 264 and inner member to revolve about axis 218, due to the rigid connection between these components. (Alternatively, a slip joint could be provided, e.g., between inner member 260 and actuator 264.) The flexibility of inner member 260 permits it to turn freely about axis 218 and to transmit the rotation through bend region 220 to ball 270. Ball 270 responds by rolling within housing 282, thereby helping to keep inner member 260 from becoming twisted and kinked.

If excessive pressure is applied to trigger 224 (for example, if the surgeon attempts to fully close surgical tool 212 when jaws 228, 230 grasp a hard object such as a bone fragment), the preloading of pressure relief spring 280 is overcome. As a result, spring 280 compresses—while inner member 260 remains axially stationary—in response to further movement of trigger 224 toward handle 225. This prevents the excessive axial force from being applied to surgical tool 212, and reduces the risk of damage to jaws 228, 230 and pins 229, 268.

Figure 9:
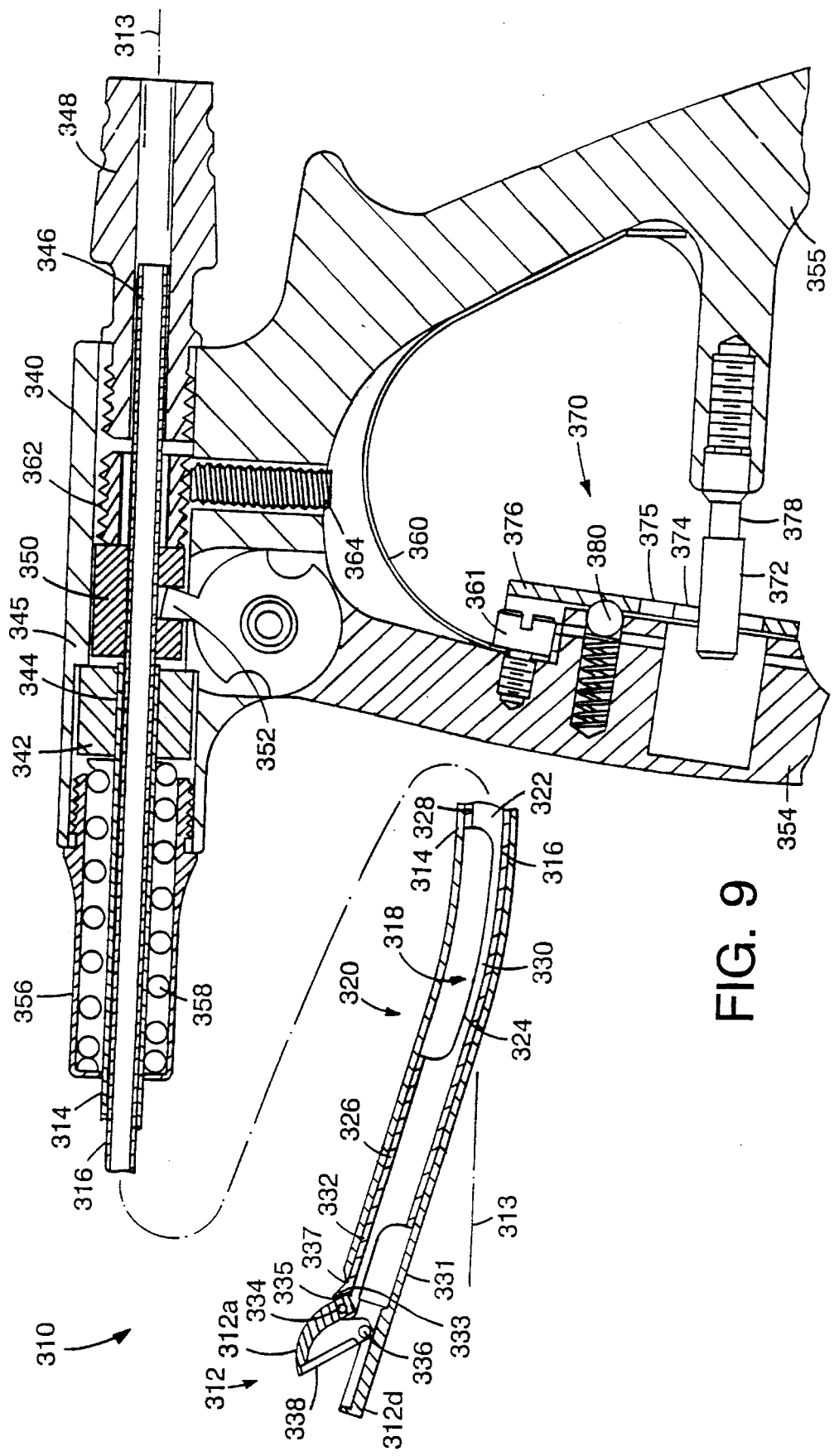
FIG. 9 is a partial cross-sectional view of portions of a surgical instrument according to yet another embodiment of the invention.

Still other embodiments are possible. For example, referring to FIG. 9, surgical instrument 310 is a "punch" arthroscopic instrument with a rotationally fixed surgical tool 312 supported by a curved stationary tube 314 and operated by an inner tube 316 coaxially disposed within tube 314. Inner tube 316 is constructed similar to inner tube 34 of surgical instrument 10, and includes a flexible region 318 that accepts the curvature imposed by a bend region 320 and allows tube 316 to slide within outer tube 314 and transmit applied axial forces to operate surgical tool 312. Tissue cut by surgical tool 312 is removed from the surgical site through a suction passage 322 in inner tube 316.

Flexible region 318 includes an axially elongated slot 324 that lies completely within bend region 320 during operation. Distal and proximal regions 326, 328 of tube 316 are rigid. The length and depth of slot 324 are selected according to the criteria set forth above for surgical instrument 10 to provide a leaf spring 330 that has adequate axial stiffness to transmit the applied axial forces through bend region 320, and yet is sufficiently flexible to slide within bend region 320 without becoming overly stressed. Inner tube 316 is oriented radially within outer tube so that leaf spring 330 is disposed opposite to the direction in which bend region 320 curves away from longitudinal axis 313, as discussed above. This helps ensure that leaf spring 330 will be supported by the walls of outer tube 314 as it slides.

Distal end 326 of inner tube 316 includes a tang-shaped extension 332 that pivotally engages a movable jaw 312a of surgical tool 312 through pin 334. Jaw 312a is hinge mounted by pin 336 to a stationary jaw 312b disposed on an extension 331 of outer tube 314. (Extensions 331, 332 are stainless steel members welded to tubes 314,316, which are also made from stainless steel.) Jaws 312a, 312b include cutting edges 338 for severing tissue or other body material.

The proximal ends of tubes 314, 316 are mounted within handpiece 340. A flange 342 is brazed to the proximal end 344 of outer tube 314. Inner tube 316 extends through flange 342 and terminates in a proximal end 346 that is slidably disposed in a suction fitting 348 at the proximal end of handpiece 340. A bracket 350 is brazed around inner tube 316 slightly proximally of flange 342. Bracket 350 is notched to receive a pin 352 on trigger 354. Tubes 314, 316, flange 342, and bracket 350 are secured within handpiece 340 by a sleeve 356, which threads into housing 340 to compress a spring 358 and flange 342 against a shoulder 345 within handpiece 340.

A return spring 360 (held in position by set screw 361) biases trigger 354 away from a stationary handle 355 to urge bracket 350 (and hence inner tube 316) proximally, thereby opening jaws 312a, 312b. A backstop 362, the position of which is threadably adjustable within the proximal end of handpiece 340, limits the amount by which jaws 312a, 312b can open by limiting the travel of bracket 350. A set screw 364 locks backstop 362 in place.

In operation, the surgeon closes and opens jaws 312a, 312b simply by squeezing and releasing trigger 354. As trigger 354 is drawn toward handle 355, pin 352 slides bracket 350 distally away from backstop 362. This movement causes inner tube 316 to slide distally within outer tube 314. Flexible region 318 transmits the axial force applied when trigger 354 is squeezed through bend region 320, thereby driving extension 332 forward and pivoting jaw 312a downwardly about pin 336. An enlarged shoulder 333 on extension 332 engages a shoulder 335 on jaw 312a in the same manner as that shown in FIG. 6 to reduce the stresses imposed on pins 334, 336. Fragments of body material severed by the operation of jaws 312a, 312b (and irrigation fluid) are drawn into transport passage 322 for removal from the surgical site by suction applied to fitting 348.

When the surgeon releases trigger 354, return spring 360 causes trigger 354 to pull inner tube 316 in the opposite direction, thereby pivoting jaw 312a upwardly away from jaw 312b. Sloped upper surface 337 of extension 332 allows extension 332 to be withdrawn within outer tube 316. Tang-shaped extension 332 flexes downwardly by a slight amount as it enters tube 314.

Handpiece 340 also includes a locking assembly 370 for allowing instrument 310 to be stored with jaws 312a, 312b closed to reduce the risk of damage to surgical tool 312 or injury due to accidental contact with cutting surfaces 338. A rod 372 on handle 355 protrudes into trigger 354 through a slot 374 on a slidable plate 376; slot 374 narrows to an upper portion 375 that is only slightly larger than a small throat 378 of rod 372. When trigger 354 is fully closed, throat 378 is aligned with slot 374. Thus, by sliding plate 376 downwardly, the user positions narrow portion 375 of slot 374 over throat 378, thereby capturing trigger 354 in the closed position. A spring-loaded ball 380 on trigger 354 engages a corresponding recess in plate 376 to hold plate 376 in its upper position when locking is not desired.

While the invention has been described in terms of surgical instruments for arthroscopy, the invention may also be used with other types of instruments, for example, instruments configured for other kinds of endoscopic procedures and for biopsy applications.

Still other embodiments are within the scope of the claims.

What is claimed is:

1. A surgical instrument comprising a stationary member disposed generally along an axis and including a bend region that angularly offsets a distal region of said stationary member from said axis, an assembly including a driver member and a generally rigid movable member that extend along said stationary member and are movable with respect to each other, said driver member having a distal end coupled to a surgical too including a first element and a second element engaged with said first element, said driver member being relieved with a first opening pattern to render it at least partially flexible for transmitting a first force applied at a proximal region of said instrument through said bend region of said stationary member to operate said surgical tool, said first element being stationary with respect to said distal region when said surgical tool is operated by applying said first force, and said generally rigid movable member having a distal end coupled to said surgical tool to carry and support said first element of said surgical tool thereat, said movable member being relieved with a second opening pattern different from said first opening pattern to provide a relatively flexible region axially aligned with said bend region proximally of said surgical tool for transmitting a second, different force applied at said proximal region through said bend region to rotate said first element and said second element with respect to said stationary member to selectively change a rotational orientation of said surgical tool with respect to said stationary member.

2. The instrument of claim 1 wherein said first element and said second element each comprises a jaw having tissue cutting edges, said second element being adapted to pivot with respect to said first element in response to said first force to move toward and closely past said first element thereby to cut tissue engaged by said cutting edges.

3. A surgical instrument comprising a stationary member including a tube, said stationary member being disposed generally along an axis and including a bend region that angularly offsets a distal region of said stationary member from said axis, an assembly including a driver member disposed within said stationary member and a generally rigid movable member, said driver member and said movable member extending along said stationary member and being movable with respect to each other, said driver member including a hollow tube and having a distal end coupled to a surgical tool, said driver member being relieved with a first opening pattern disposed with in said bend region, said first opening pattern rendering said driver member at least partially flexible for transmitting a first force applied at a proximal region of said instrument through said bend region of said stationary member to operate said surgical tool, said first opening pattern including an axially elongated opening in a wall of said tube of said driver member, said elongated opening extending a selected amount axially along said tube and extending radially over at least 60% of a diameter of said tube and said generally rigid movable member having a distal end coupled to said surgical tool and being relieved with a second opening pattern different from said first opening pattern to provide a relatively flexible region axially aligned with said bend region proximally of said surgical tool for transmitting a second, different force applied at said proximal region through said bend region to selectively change a rotational orientation of said surgical tool with respect to said stationary member.

4. A surgical instrument comprising a stationary member including a tube, said stationary member being disposed generally along an axis and including a bend region that angularly offsets a distal region of said stationary member from said axis, an assembly including a driver member disposed within said stationary member and a generally rigid movable member, said driver member and said movable member extending along said stationary member and being movable with respect to each other, said driver member including a hollow tube and having a distal end coupled to a surgical tool, said driver member being relieved with a first opening pattern disposed with in said bendregion, said first opening pattern rendering said driver member at least partially flexible for transmitting a first force applied at a proximal region of said instrument through said bend region of said stationary member to operate said surgical tool, said first opening pattern including an axially elongated opening in a wall of said tube of said driver member, said elongated opening extending a selected amount axially along said tube and extending radially over at least 75% of a diameter of said tube and said generally rigid movable member having a distal end coupled to said surgical tool and being relieved with a second opening pattern different from said first opening pattern to provide a relatively flexible region axially aligned with said bend region proximally of said surgical tool for transmitting a second, different force applied at said proximal region through said bend region to selectively change a rotational orientation of said surgical tool with respect to said stationary member.

5. A surgical instrument comprising a stationary member including a tube, said stationary member being disposed generally along an axis and including a bend region that angularly offsets a distal region of said stationary member from said axis, an assembly including a driver member disposed within said stationary member and a generally rigid movable member, said driver member and said movable member extending along said stationary member and being movable with respect to each other, said driver member having a distal end coupled to a surgical tool including a first element carried by said movable member and a second element, said driver member being relieved with a first opening pattern disposed with said bend region, said first opening pattern rendering said driver member at least partially flexible for transmitting a first force applied at a proximal region of said instrument through said bend region of said stationary member to operate said surgical tool, said second element being adapted to be moved by said driver member with respect to said first element of said tool in response to said first force to operate said surgical tool, and said generally rigid movable member having a distal end coupled to said surgical tool and being relieved with a second opening pattern different from said first opening pattern to provide a relatively flexible region axially aligned with said bend region proximally of said surgical tool for transmitting a second, different force applied at said proximal region through said bend region to selectively change a rotational orientation of said surgical tool with respect to said stationary member.

6. The instrument of claim 5 wherein said first element and said second element each comprises a jaw having tissue cutting edges, said second element being adapted to pivot with respect to said first element in response to said first force to move toward and closely past said first element thereby to cut tissue engaged by said cutting edges.

7. The instrument of claim 6 wherein said driver member includes a passage disposed therein for transporting tissue fragments cut by said surgical tool through said instrument in response to suction applied to a proximal region of said driver member.

8. The instrument of claim 6 wherein said first force is applied axially and said driver member is adapted to slide axially toward said distal region in response to said first force to close said jaws.

9. A surgical instrument comprising a stationary member disposed generally along an axis and including a bend region that angularly offsets a distal region of said stationary member from said axis, an assembly including a driver member and a generally rigid movable member that extend along said stationary member and are movable with respect to each other, said driver member having a distal end coupled to a surgical tool and being relieved with a first opening pattern to render it at least partially flexible for transmitting a first force applied at a proximal region of said instrument through said bend region of said stationary member to operate said surgical tool, and said generally rigid movable member having a distal end coupled to said surgical tool and being relieved with a second opening pattern different from said first opening pattern to provide a relatively flexible region axially aligned with said bend region proximally of said surgical tool for transmitting a second, different force applied at said proximal region in a rotational direction with respect to said axis, through said bend region to selectively change a rotational orientation of said surgical tool with respect to said stationary member, said assembly being constructed to allow said movable member to rotate in response to said second force and change said rotational orientation of said surgical tool without disrupting the ability of said driver member to operate said surgical tool, said driver member remaining substantially rotationally stationary with respect to said bend region as said movable member rotates said surgical tool.

10. A surgical instrument comprising a stationary member disposed generally along an axis and including a bend region that angularly offsets a distal region of said stationary member from said axis, an assembly including a driver member and a generally rigid movable member that extend along said stationary member and are movable with respect to each other, said driver member having a distal end coupled to a surgical tool and being relieved with a first opening pattern to render it at least partially flexible for transmitting a first force applied at a proximal region of said instrument through said bend region of said stationary member to operate said surgical tool, and said generally rigid movable member having a distal end coupled to said surgical tool and being relieved with a second opening pattern different from said first opening pattern to provide a relatively flexible region axially aligned with said bend region proximally of said surgical tool for transmitting a second, different force, applied at said proximal region in a rotational direction with respect to said axis, through said bend region to selectively change a rotational through said bend region to selectively change a rotational orientation of said surgical tool with respect to said stationary member, said assembly being constructed to allow said movable member to rotate in response to said second force and change said rotational orientation of said surgical tool without disrupting the ability of said driver member to operate said surgical tool, said surgical tool including a first element carried by and rotatable with said movable member and a second element actuated by said driver member with respect to the first element to operate said tool, said first element engaging said second element to cause said second element to rotate with said first element in response to said second force, said driver member remaining substantially rotationally stationary with respect to said bend region as said first element and said second element rotate.

11. The instrument of claim 10 further comprising a rotational joint disposed between a distal end of said driver element and said second element to allow said driver member to remain substantially rotationally stationary with respect to said bend region as said first element and said second element rotate.

12. A surgical instrument comprising a stationary member disposed generally along an axis and including a bend region that angularly offsets a distal region of said stationary member from said axis, an assembly including a driver member and a generally rigid movable member that extend along said stationary member and are movable with respect to each other, said driver member having a distal end coupled to a surgical tool and being relieved with a first opening pattern to render it at least partially flexible for transmitting a first force applied at a proximal region of said instrument through said bend region of said stationary member to operate said surgical tool, and said generally rigid movable member having a distal end coupled to said surgical tool and being relieved with a second opening pattern different from said first opening pattern to provide a relatively flexible region axially aligned with said bend region proximally of said surgical tool for transmitting a second, different force, applied at said proximal region in a rotational direction with respect to said axis, through said bend region to selectively change a rotational orientation of said surgical tool with respect to said stationary member, said assembly being constructed to allow said movable member to rotate in response to said second force and change said rotational orientation of said surgical tool without disrupting the ability of said driver member to operate said surgical tool, said driver member being rotatably coupled to said surgical tool to rotate with said surgical tool in response to rotation of said movable member.

13. A surgical instrument comprising a stationary member disposed generally along an axis and including a bend region that angularly offsets a distal region of said stationary member from said axis, an assembly including a driver member and a generally rigid movable member that extend along said stationary member and are movable with respect to each other, said driver member having a distal end coupled to a surgical tool and being relieved with a first opening pattern to render it at least partially flexible for transmitting a first force applied at a proximal region of said instrument through said bend region of said stationary member to operate said surgical tool, and said generally rigid movable member having a distal end coupled to said surgical tool and being relieved with a second opening pattern different from said first opening pattern to provide a relatively flexible region axially aligned with said bend region proximally of said surgical tool for transmitting a second, different force, applied at said proximal region through said bend region to selectively change a rotational orientation of said surgical tool with respect to said stationary member, and a manual actuator disposed at said proximal region of said instrument for supporting said stationary member and coupled to a proximal region of said assembly for applying said first force to said assembly to operate said surgical tool, and means for decoupling said actuator from said assembly if said first force exceeds a threshold thereby to avoid applying excessive force to said surgical tool.

14. The instrument of claim 13 wherein said means for decoupling includes a spring for coupling said actuator to said proximal region of said assembly, said spring being constructed to transmit said first force to said assembly if said first force is below said threshold and to compress in response to forces that exceed said threshold to avoid applying said excessive force to said assembly.

15. A surgical instrument comprising a stationary member supporting a surgical tool at a distal region thereof, a rotatable member supported by said stationary member and having a distal end coupled to said surgical tool and being relieved with a first opening pattern to render it at least partially flexible for transmitting rotational force applied at a proximal region of said instrument to said surgical tool to selectively change a rotational orientation of said surgical tool with respect to said stationary member, a driver member supported by said stationary member and having a distal end coupled to said surgical tool and being relieved with a second pattern different from said first opening pattern to render it at least partially flexible for transmitting an axial force applied at said proximal region to said surgical tool to operate said surgical tool and cause said surgical tool to sever body material, and one of said rotatable member or said driver member being hollow to provide a passage that extends from a distal end of said one member proximally through said one member to said proximal region of said instrument for transporting body material severed by said surgical tool from said distal region to said proximal region of said instrument in response to suction applied at said proximal region of said instrument.

16. The instrument of claim 15 wherein said stationary member is generally disposed along an axis and includes a bend region to offset said distal region from said axis.

17. The instrument of claim 16 wherein said stationary member comprises a tube, wherein said rotatable member includes a generally rigid tube disposed within said stationary member and wherein said first opening pattern is disposed within said bend region.

18. The instrument of claim 16 wherein said stationary member comprises a tube, wherein said driver member includes a generally rigid tube disposed within said stationary member and wherein said second opening pattern is disposed within said bend region.

19. The instrument of claim 18 wherein said passage is disposed through said driver member.

20. The instrument of claim 16 further comprising means for allowing said surgical tool to be rotated by said rotatable member to change said rotational orientation without disrupting the ability of said driver member to operate said surgical tool.

21. The instrument of claim 20 wherein said stationary member comprises a tube, and wherein said rotatable member includes a generally rigid tube, said means for allowing including means for holding said driver member substantially rotationally stationary with respect to said bend region as said surgical tool rotates.

22. The instrument of claim 15 wherein said stationary member includes an open distal end, said stationary member supporting said surgical tool distally of said distal end, and further comprising means for axially securing said surgical tool to said distal end without interfering with rotatable member changing said rotational orientation or said driver member operating said surgical tool.

23. The instrument of claim 22 wherein said axially securing means includes a collar threadably received by said distal end for capturing at least a portion of said surgical tool, said collar axially securing said surgical tool to said distal end and permitting said tool to rotate within said collar.

24. A surgical instrument comprising a stationary member disposed generally along an axis and including a bend region that angularly offsets a distal region of said stationary member from said axis, a surgical tool disposed at said distal region, and a movable member supported by said stationary member, said movable member having a generally rigid distal region coupled to said surgical tool, a generally rigid proximal region disposed at a proximal region of said instrument, and a flexible intermediate region disposed in said bend region, said flexible region including an axially elongated strip of material rigidly interconnected at either end to said generally rigid distal region and said generally rigid proximal region, said strip of material being circumferentially bounded by an axially elongated opening disposed between said generally rigid distal region and said generally rigid proximal region, said strip of material being sufficiently axially stiff to transmit to axial force applied to said proximal region of said movable member through said bend region of said stationary member to operate said tool, said movable member being disposed to slide within said stationary member in response to said applied axial force.

25. The instrument of claim 24 wherein said movable member comprises a hollow tube, a portion of said tube being relieved to provide said elongated opening and axially elongated strip of material.

26. A surgical instrument comprising a stationary member disposed generally along an axis and including a bend region that angularly offsets a distal region of said stationary member from said axis, a surgical tool disposed at said distal region, and a movable member supported by said stationary member, said movable member having a generally rigid distal region coupled to said surgical tool, a generally rigid proximal region disposed at a proximal region of said instrument, and a flexible intermediate region disposed in said bend region, said flexible region including an axially elongated strip of material rigidly interconnected at either end to said generally rigid distal region and said generally rigid proximal region, said strip of material being circumferentially bounded by an axially elongated opening disposed between said generally rigid distal region and said generally rigid proximal region, said strip of material being sufficiently axially stiff to transmit an axial force applied to said proximal region of said movable member through said bend region of said stationary member to operate said tool, said axially elongated strip of material having a length selected so that said generally rigid distal and proximal regions of said movable member disposed adjacent to said flexible remain substantially outside of said bend region during operation of said tool.

27. A surgical instrument comprising a stationary member disposed generally along an axis and including a bend region that angularly offsets a distal region of said stationary member from said axis, a surgical tool disposed at said distal region, and a tubular movable member supported by said stationary member, said movable member having a generally rigid distal region coupled to said surgical tool, a generally rigid proximal region disposed at a proximal region of said instrument, and a flexible intermediate region disposed in said bend region, said flexible region including an axially elongated strip of material rigidly interconnected at either end to said generally rigid distal region and said generally rigid proximal region, said strip of material being circumferentially bounded by an axially elongated opening disposed extending radially into said tubular moveable member by a selected amount and disposed between said generally rigid distal region and said generally rigid proximal region, said strip of material being sufficiently axially stiff to transmit an axial force applied to said proximal region of said movable member through said bend region of said stationary member to operate said tool.

28. The instrument of claim 27 wherein said elongated opening radially extends over at least 60% of a diameter of said tube.

29. The instrument of claim 27 wherein said elongated opening radially extends over at least 75% of a diameter of said tube.

30. A surgical instrument comprising a stationary member disposed generally along an axis and including a bend region that angularly offsets a distal region of said stationary member from said axis, a surgical tool disposed at said distal region, and a movable member supported by said stationary member, said movable member having a generally rigid distal region coupled to said surgical tool, a generally rigid proximal region disposed at a proximal region of said instrument, and a flexible intermediate region disposed in said bend region, said flexible region including an axially elongated strip of material rigidly interconnected at either end to said generally rigid distal region and said generally rigid proximal region, said strip of material being circumferentially bounded by an axially elongated opening disposed between said generally rigid distal region and said generally rigid proximal region, and said strip of material being sufficiently axially stiff to transmit an axial force applied to said proximal region of said movable member through said bend region of said stationary member to operate said tool, said elongated opening having a length selected so that said generally rigid distal and proximal regions of said tube disposed adjacent to said elongated opening remain substantially outside of said bend region during operation of said surgical tool.

31. A surgical instrument comprising a stationary member disposed generally along an axis and including a bend region that angularly offsets a distal region of said stationary member from said axis, a surgical tool disposed at said distal region, and a movable member supported by said stationary member, said movable member having a generally rigid distal region coupled to said surgical tool, a generally rigid proximal region disposed at a proximal region of said instrument, and a flexible intermediate region disposed in said bend region, said flexible region including an axially elongated strip of material rigidly interconnected at either end to said generally rigid distal region and said generally rigid proximal region, said strip of material being circumferentially bounded by an axially elongated opening disposed between said generally rigid distal region and said generally rigid proximal region, said strip of material being sufficiently axially stiff to transmit an axial force applied to said proximal region of said movable member through said bend region of said stationary member to operate said tool, a passage defined at least in part by one of said stationary member or movable member for transporting body material severed by said surgical tool from said distal region to said proximal region of said instrument in response to suction applied at said proximal region.

32. The instrument of claim 31 wherein said passage is disposed in said movable member.

33. A surgical instrument comprising a first member having a distal end coupled to a surgical tool and a region relieved with a first opening pattern to render it relatively flexible, a second member carried by said first member and movable with respect to said first member, said second member having a distal end coupled to said surgical tool and a region relieved with a second opening pattern different from said first opening pattern to render it relatively flexible, a stationary member disposed generally along an axis, said stationary member carrying said first member and said second member and having a bend region that angularly offsets a distal region of said stationary member from said axis, said first member being disposed inside said stationary member with the relieved region of said first member being disposed within said bend region.

34. The surgical instrument of claim 33 wherein said second member is disposed inside said first member with the relieved region of said second member being disposed within said bend region.

* * * * *

UNITED STATES PATENT AND TRADEMARK OFFICE
CERTIFICATE OF CORRECTION

PATENT NO.   : 5,620,415

DATED         : April 15, 1997

INVENTOR(S) : Paul V. Lucey et al.

It is certified that error appears in the above-identified patent and that said Letters Patent is hereby corrected as shown below:

ON THE TITLE PAGE:

Item [56] References Cited, U.S. Patent Documents:
Replace "274,096 5/1883 Shutt" with --Des. 274,096 05/1984 Shutt--.

Replace "5,333,502 08/1994" with "5,330,502 07/1994".

Col. 2, line 52, replace "rotasable" with --rotatable--;
        line 53, replace "witch, in" with --within--.

Col. 3, line 37, replace "a" (first occurrence) with --an--.

Col. 4, line 38, replace "ore" with --one--.

Col. 5, line 39, replace "34" with --32--;
        line 66, replace "232" with --32--.

Col. 6, line 62, delete "shaped," (second occurrence).

Col. 10, line 5, replace "212" with --12--.

Col. 11, line 27, replace "shown" with --show--.

Col. 16, claim 1, line 31, replace "too" with --tool--.

UNITED STATES PATENT AND TRADEMARK OFFICE
CERTIFICATE OF CORRECTION

PATENT NO.   : 5,620,415
DATED        : April 15, 1997
INVENTOR(S)  : Paul V. Lucey et al.

It is certified that error appears in the above-identified patent and that said Letters Patent is hereby corrected as shown below:

Col. 17, claim 3, line 7, replace "with in" with --within--.

Col. 18, claim 5, line 8, replace "with" with --within--.

Col. 19, claim 10, lines 28-29, delete "through said bend region to selectively change a rotational--.

Col. 20, claim 13, line 34, replace "force," with --force--.

Col. 22, claim 24, line 6, replace "to"(second occurrence) with --an--.

Col. 22, claim 26, line 40, after "flexible" insert --region--.

Col. 22, claim 27, line 60, delete "disposed".

Signed and Sealed this

Twelfth Day of May, 1998

Attest:

BRUCE LEHMAN

Attesting Officer         Commissioner of Patents and Trademarks